(12) United States Patent
Li

(10) Patent No.: US 7,642,508 B2
(45) Date of Patent: *Jan. 5, 2010

(54) MICRO FLUIDIC GAS ASSISTED IONIZATION STRUCTURE AND METHOD

(75) Inventor: Gangqiang Li, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 11/680,577

(22) Filed: Feb. 28, 2007

(65) Prior Publication Data

US 2007/0257190 A1 Nov. 8, 2007

Related U.S. Application Data

(63) Continuation-in-part of application No. 11/429,085, filed on May 4, 2006, now Pat. No. 7,495,210.

(51) Int. Cl.
H01J 49/00 (2006.01)
B01D 59/44 (2006.01)
(52) U.S. Cl. .................. 250/281; 250/282; 250/288; 250/425
(58) Field of Classification Search ........... 250/281, 250/282, 288, 425
See application file for complete search history.

(56) References Cited

U.S. PATENT DOCUMENTS

| 7,070,682 | B2 | 7/2006 | Lee et al. | |
|---|---|---|---|---|
| 7,462,825 | B2 * | 12/2008 | Miller et al. | 250/288 |
| 7,495,210 | B2 * | 2/2009 | Li | 250/288 |
| 2003/0026740 | A1 | 2/2003 | Staats | |
| 2004/0023740 | A1 | 2/2004 | Benassi et al. | |
| 2006/0027744 | A1 | 2/2006 | Stults et al. | |
| 2006/0060769 | A1 | 3/2006 | Bousse et al. | |
| 2006/0242832 | A1 | 11/2006 | Weng et al. | |

FOREIGN PATENT DOCUMENTS

| WO | WO 97/04297 A1 | 2/1997 |
|---|---|---|
| WO | WO 00/41214 A1 | 7/2000 |
| WO | WO 2004/051697 A3 | 6/2004 |
| WO | WO 2005/019804 A3 | 3/2005 |

OTHER PUBLICATIONS

UK Intellectual Property Office, Patents Act: 1977 Search Report under Section 17, Aug. 15, 2007.

* cited by examiner

*Primary Examiner*—Nikita Wells

(57) ABSTRACT

In accordance with the invention, auxiliary structures are used in conjunction with a microfluidic chip to form a microfluidic electrospray structure that allows gas assisted nebulization for use in a mass spectrometry system.

15 Claims, 9 Drawing Sheets

MICRO FLUIDIC GAS ASSISTED IONIZATION STRUCTURE AND METHOD

CROSS-REFERENCE TO RELATED APPLICATIONS

This application is a continuation in part of U.S. Ser. No. 11/429,085 filed May 4, 2006 now U.S. Pat. No. 7,495,210 by the same inventor and assigned to the same assignee.

BACKGROUND

Atmospheric pressure ionization (API) methods have been widely used to couple chromatographic separations such as high performance liquid chromatograph (LC) or capillary electrophoresis (CE) to mass spectrometers for chemical and biochemical sample analysis. In such systems, the sample effluent from a LC, for instance, is delivered to a capillary placed near the mass spectrometer inlet or interface. By applying a potential difference between the capillary and interface, charge droplets are generated in a continuous spray. Charged droplets further undergo a desolvation process and ion species are generated for mass spectrometry analysis.

Collisions between gas molecules and solution facilitate generation of fine droplets. In nanospray techniques it has been common to use direct nebulization without a gas assist. Both pneumatic and direct nebulization methods provide relatively stable spray ionization in case sample effluent contains high concentration of organic solvent. However, for analytes having a higher water content it is typically more difficult to form stable spray in a direct nebulization source. Electrospray generated by direct nebulization also typically contains relatively large droplet which are more likely to be incompletely desolvated before entering the mass spectrometer. Consequently, high signal to noise is typically observed.

SUMMARY OF THE INVENTION

In accordance with the invention, auxiliary structures are used in conjunction with a microfluidic chip to form a microfluidic electrospray structure that allows gas assisted nebulization for use in a mass spectrometry system

BRIEF DESCRIPTION OF THE FIGURES

The invention is described in detail below with reference to the following figures.

DETAILED DESCRIPTION

Before describing the invention in detail, it is be noted that, as used in this specification and the appended claims, the singular forms "a," "an," and "the" include plural referents unless the context clearly dictates otherwise. Thus, for example, reference to "a microfluidic chip" includes more than one "microfluidic chip". Reference to a "central layer" includes more than one "central layer". In describing and claiming the present invention, the following terminology will be used in accordance with the definitions set out below.

The term "adjacent" means, near, next to or adjoining. Something adjacent may also be in contact with another component, intersect the other component, surround the other component, be spaced from the other component or contain a portion of the other component. For instance, a gas channel that is adjacent to an analyte channel may be spaced next to the channel, may contact the channel, or may surround or be surrounded by the channel, may contain, may adjoin the channel or may be near the channel.

The term "detector" refers to any device, apparatus, machine, component, or system that can detect an ion. Detectors may or may not include hardware and software. In a mass spectrometer the common detector includes and/or is coupled to a mass analyzer.

The term "mass spectrometry system" refers to a system comprising at least a micro fluidic chip, an optional ion transport system, a mass analyzer and a detector.

The term "mass analyzer" refers to any number of mass analyzers known in the art for identifying, separating and characterizing molecules.

The term "separation system" refers to any analytical or preparative apparatus that may be used or employed to separated purify or concentrate molecules that will be introduced into the micro fluidic chip.

The term "transport system" refers to any number of conduits, electrodes or other methods known and used in the art for moving molecules from one place to another.

The embodiments in accordance with the invention are described with reference to the figures. The figures are not to scale, and in particular, certain dimensions may be exaggerated for clarity of presentation.

Figure 1:
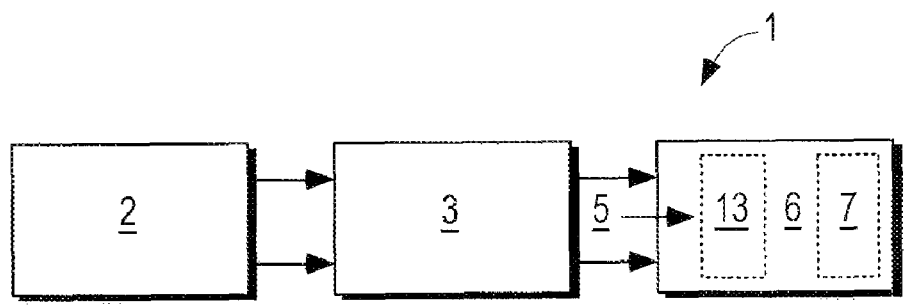
FIG. 1 shows a general block diagram of the system in accordance with the invention.

FIG. 1 shows a general block diagram of analytical system 1 in accordance with the invention. Analytical system 1 may comprise optional separation system 2, microfluidic chip 3, an optional transport system 5 and mass spectrometry system 6. Mass spectrometry system 6 comprises mass analyzer 13 and detector 7. The block diagram is not to scale and is drawn in a general format because embodiments in accordance with the invention may be used with a variety of different types of designs and systems. In addition, each of the designs or arrangements may be changed or adjusted. The invention should not be interpreted to be limited to the illustrated embodiments. Each of the systems and/or components will be described in more detail below.

Optional separation system 2 may comprise any number of systems known in the art for separating molecules. More commonly this system may comprise an analytical system such as a liquid chromatography system (LC). However, other systems and methods known in the art may be employed. For instance, the separation system 2 may also comprise an electrophoresis system and/or apparatus, an isoelectric focusing system and/or apparatus, a biorad or similar type preparative electrophoresis system and/or apparatus, an analytical or preparative column, a two dimensional gel, and other systems and/or apparatus that are known in the art for separating molecules. FIG. 1 shows an embodiment in accordance with the invention where an analytical system is employed. The analytical system, for example, comprises a high performance liquid chromatography (HPLC) microfluidic chip and associated equipment. These parts and designs are well known in the art and are, therefore, not described here in any further detail.

FIGS. 2-5 show more detailed views of microfluidic chip 3 of the present invention. Microfluidic chip 3 may comprise a single substrate or one or more layers of material (single substrate not shown in drawings). In the case of the embodiment using layers, the layers may be joined or bonded or designed to be fastened or attached in place. Referring to FIGS. 2-5, microfluidic chip 3 comprises first outer layer 11, central layer 13, and second outer layer 14. Central layer 13 contacts first outer layer 11 and second outer layer 14. One or more optional outer layers (not shown in FIGS) may be employed and contact second outer layer 14 or first outer layer 11. Other layers and designs or embodiments are possible. The invention should not be interpreted to be limited to the described embodiments. For instance, it can be imagined that a plurality of differing layers may be employed. In addition, the layers may be in differing orientations, stacking arrangements or positions. Microfluidic chip 3 has first end 9 with spray tip 10. Microfluidic chip 3 and/or central layer 13 comprise analyte channel 15, first gas channel 17 and second gas channel 19.

First outer layer 11 may comprise any number of materials known or employed in the art. For instance, first outer layer 11 may comprise a polyimide material or other type polymer that may be constructed in a defined arrangement for bonding or attaching the other layers. Each of the layers may be designed of varying compositions and thicknesses. Layers may comprise composite materials, polymers, plastics, metals, stainless steel, semiconductor materials, or any other material known in the art. Other materials not known in the art may also be employed that are capable of being etched or designed with a channel in or through the material.

Central layer 13 may comprise any number of materials known or employed in the art. For instance, Central layer 13 may comprise a polyimide material or other type polymer that may be constructed in a defined arrangement for bonding or attaching the other layers. Central layer 13 may be designed or constructed to attach or be joined to first outer layer 11. Fasteners and adhesives known in the art may be employed to join central layer 13 and first outer layer 11. Each of the layers may be designed of varying compositions and thicknesses. Layers may comprise composite materials, polymers, plastics, metals, stainless steel, titanium, semiconductor materials, or any other material known in the art. Other materials not known in the art may also be employed that are capable of being etched or designed with a channel in or through the material.

Second outer layer 14 may comprise any number of materials known or employed in the art. For instance, second outer layer 14 may comprise a polyimide material or other type polymer that may be constructed in a defined arrangement for bonding or attaching the other layers. Second outer layer 14 and/or central layer 13 may be designed to attach together or be joined. Adhesives know in the art may also be employed for joining second outer layer 14 to central layer 13.

Each of the layers may be designed of varying compositions and thicknesses. Layers may comprise composite materials, polymers, plastics, metals, stainless steel, titanium, semiconductor materials, or any other material known in the art. Other materials not known in the art may also be employed that are capable of being etched or designed with a channel in or through the material.

Transport system 5 is used for transporting ions and moving them from one location to another. Transport system 5 is typically interposed between microfluidic chip 3 and mass spectrometry system 6. However, this is not a required configuration.

Transport system 5 may comprise any number of ion transporting devices known in the art. Typically, some type of skimmer or ion optics guide may also be employed in transport system 5. Transport systems 5 are well known in the art and are, therefore, not discussed in detail here.

Mass spectrometry system 6 comprises mass analyzer 13 and detector 7 mass analyzer 13 is used for separating and determining the m/z ratio of the ions produced by an ion source. In certain instances mass spectrometry system 6 may also comprise microfluidic chip 3.

Detector 7 is positioned downstream from transport system 15 and may comprise any number of detectors known and used in the art. Some typical detectors may include photomultiplier tubes or other similar type technology. The detectors may be coupled to a computer and interface for output of the results to a third party user interface (not shown in the FIGS.).

Figure 2:
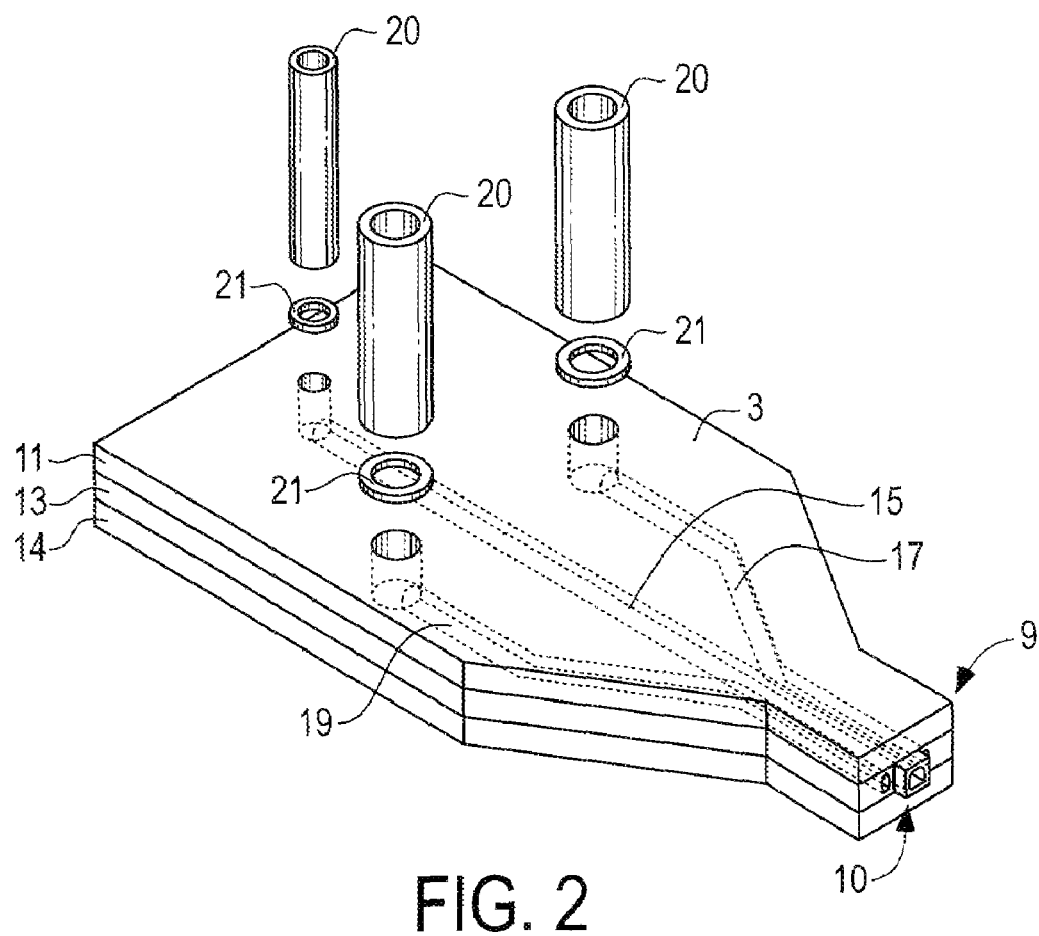
FIG. 2 shows a perspective view of an embodiment in accordance with the invention.
Figure 3:
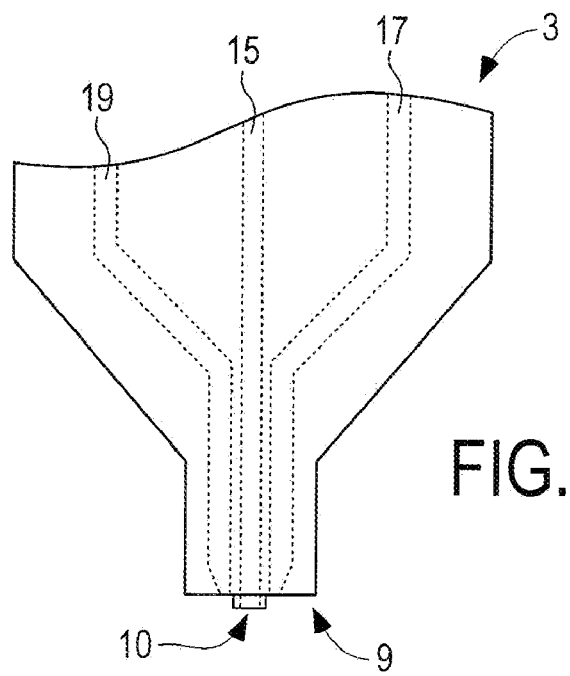
FIG. 3 shows a plan view of an embodiment in accordance with the invention.

FIG. 2 shows a perspective view of microfluidic chip 3 in accordance with the invention. FIG. 2 shows additional details of analyte channel 15, first gas channel 17 and second gas channel 19. A series of one or more connection conduits 20 and/or sealing gaskets 21 may be employed in accordance with the invention for coupling microfluidic chip 3 to one or more analyte and/or gas sources. It should be noted that other channels may be employed in accordance with the invention. In no case should the present embodiments be interpreted to limit the scope of the invention. For instance, various number and channels with differing orientations, designs, volumes and valves may also be employed in accordance with the invention. It can be imagined that a series of valves may also be employed to assist in chemical reactions and mixing. Various valves can be designed to open and close in varying channels to promote mixing of molecules at various stoichiometric amounts. Each of the channels may also be designed for carrying various volumes, flow rates and pressures. These parameters can be further designed and improved based on the samples that are employed. The channels may be designed and/or constructed by using various techniques known in the art. For instance, the channels may be designed using laser ablation techniques, etching, or other appropriate methods know in the art. Other gas channels and embodiments may be employed. Each of the channels exit at a common end. In the diagram the first gas channel, analyte channel 15 and second gas channel 19 all exit at the first end 9. The channels end at first end 9 to define spray tip 10. The diagram shows each of the channels being oriented parallel to each other. This is not a requirement of the invention. In other embodiments or designs the channels may be, non-parallel, perpendicular, non-linear, linear or in any various arrangement in which they intersect. Various mixing or other channel or chambers may be employed with the present invention.

Figure 4:
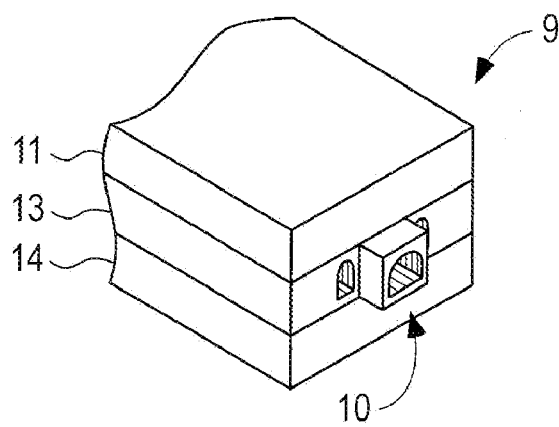
FIG. 4 shows a perspective view of an embodiment in accordance with the invention.
Figure 5:
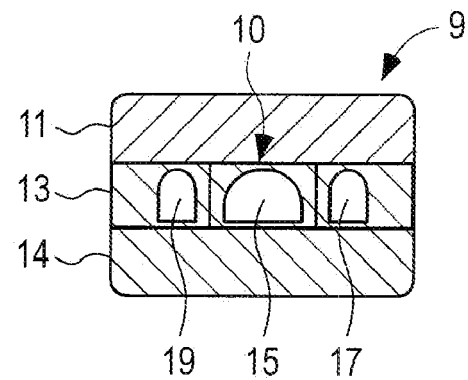
FIG. 5 shows a cross-sectional view of an embodiment in accordance with the invention.

FIGS. 4 and 5 show cross-sectional views of microfluidic chip 3 presenting accordance with the invention. FIGS. 4 and 5 show first gas channel 17, second gas channel 19 and analyte channel 15. First gas channel 17, second gas channel 19 and analyte channel 15 are disposed in central layer 13 or a portion of central layer 13. This is not a requirement of the invention. In certain embodiments it can be imagined that other analyte and/or gas channels may be employed. In certain embodiments the analyte channel 15 may be designed for conducting separations of the sample or analyte molecules. Various techniques are known in the art for building microfluidic chips for actual separations in situ. This type of design eliminates the need for optional separation system 2. However, in certain cases separation system 2 may also be employed in conjunction with analyte channel 15. This is the case when the separation system 2 performs separations of certain molecules and then analyte channel performs a follow up separation or further purification. In addition, first gas channel 17 and/or second gas channel 19 may be disposed in outer layer 11 and/or second outer layer 14 or a portion of one or more of these layers. Analyte channel 15 may be disposed in central layer 13 as shown and/or in one or more of outer layers 11 and/or 14. Analyte channel 15 may also be disposed in a portion of one or more of these layers. First gas channel 17, second gas channel 19 and analyte channel 15 may be designed in both symmetric and non-symmetric orientations relative to each other. Each of the channels is shown aligned with each other in a symmetric or parallel orientation as they extend down microfluidic chip 3. This is not a requirement. It can be imagined that each of these channels may be designed to intersect or be disposed in a non linear or non-symmetric arrangement to each other.

Figure 6A:
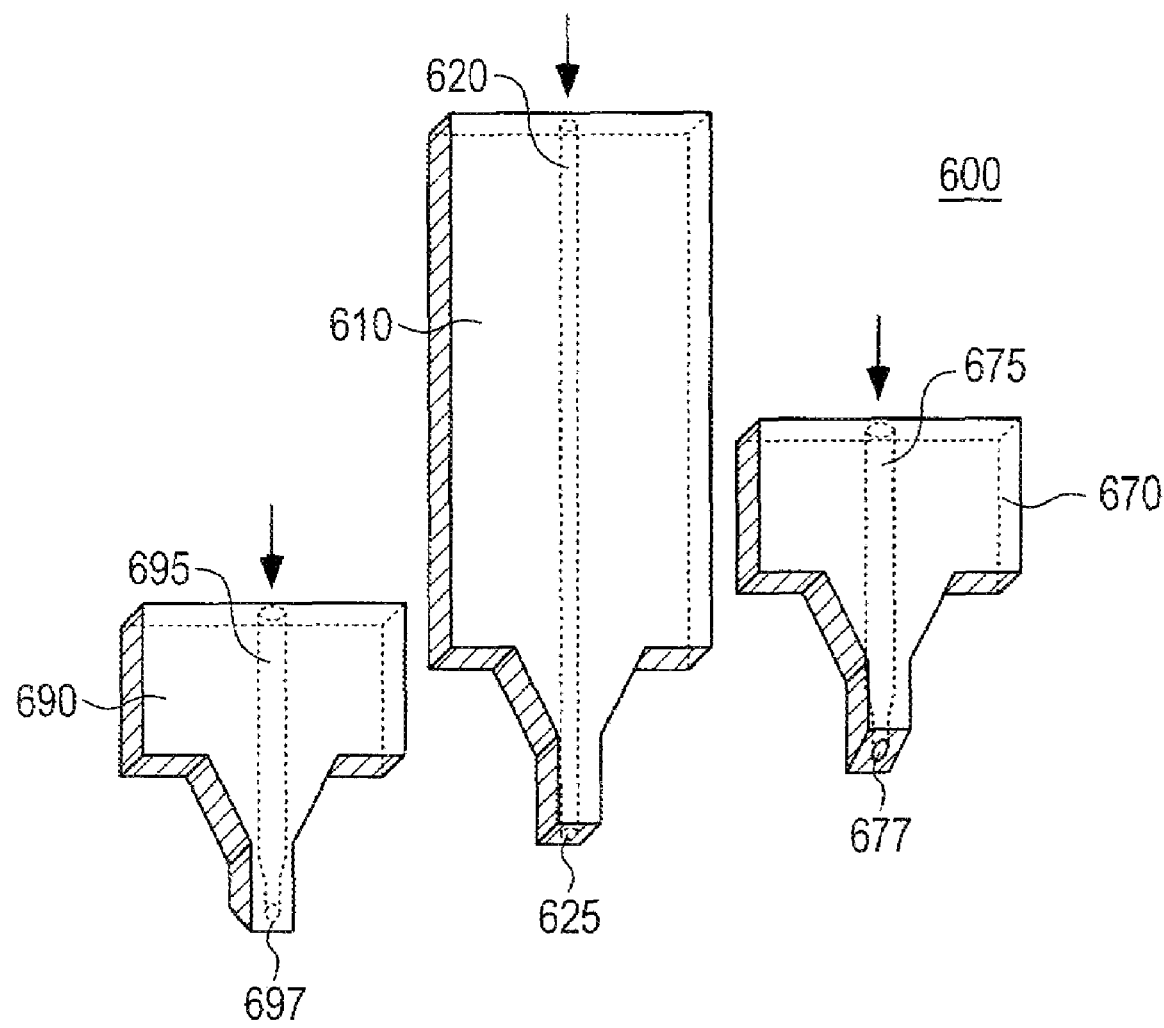
FIG. 6a shows an embodiment in accordance with the invention in an exploded view.

FIG. 6a shows an embodiment in accordance with the invention in an exploded view. The embodiment shown in FIGS. 6a-b allows microfluidic chip 610 with direct nebulization to be converted to gas assisted nebulization. Microfluidic chip 610 may be made from materials such as, for example, stainless steel, titanium, glass, polyimide or other suitable polymers. Microfluidic chip 610 comprises analyte channel 620 in the center of microfluidic chip 610 with spray tip 625 at one end of analyte channel 620. Microfluidic chip 610 typically comprises three layers (e.g., see FIG. 2) which are then bonded together using a process suitable for the material being used. For example, if polyimide is used, the layers may be laminated together to form microfluidic chip 610. Analyte channel 620 is formed in the central layer. Depending on the material, both analyte channel 620 and spray tip 625 may be formed using laser ablation or lithographic techniques. For the case where microfluidic chip 610 is formed of non-conducting material such as glass or polyimide, for example, a portion of microfluidic chip 610 is typically coated with a metal film so that a voltage may be applied to generate a spray.

Figure 6B:
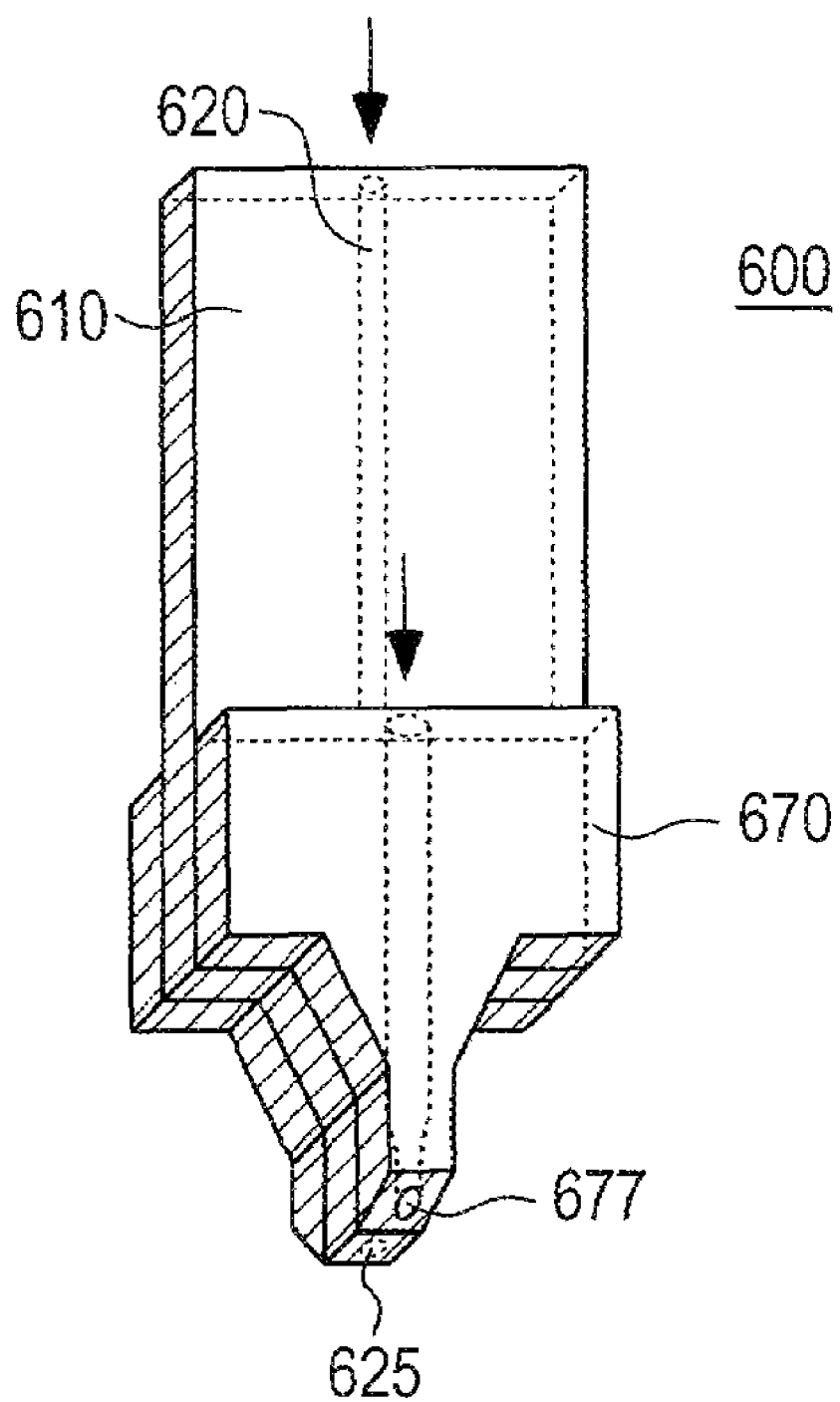
FIG. 6b shows an embodiment in accordance with the invention.

In accordance with the invention, two auxiliary gas chips 690 and 670 are disposed adjacent to and in contact with microfluidic chip 610. Typically, auxiliary gas chips 690 and 670 are made of a material similar to and have dimensions similar to that of microfluidic chip 610. Both auxiliary chips 690 and 670 have gas channels 695 and 675, respectively. Gas channels 697 and 677 each have a gas input means. Analyte channel 620 is typically the central channel in microfluidic chip 610 while gas channels 695 and 675 residing in auxiliary gas chips 690 and 670, respectively, are used for transporting the nebulization gas. Auxiliary gas chips 690 and 670 are typically placed on the top and bottom of microfluidic chip 610, respectively, and aligned with microfluidic chip 610 to form microfluidic electrospray structure 600 as shown in FIG. 6b. Auxiliary gas chips 690 and 670 may, for example, be glued or laminated onto microfluidic chip 610. The gas channel ends 697 and 677 of gas channels 695 and 675, respectively, are typically positioned about 20 μm to about 500 μm behind spray tip 625. Gas channels 695 and 675 have dimensions similar to analyte channel 620 which is typically on the order of 50 μm in diameter but the diameters at gas channel ends 697 and 677 are typically considerably smaller, on the order of about 10 μm. Because of the smaller diameter at gas channel ends 697 and 677, a pressure drop is created at gas channel ends 697 and 677 resulting in a high speed gas stream. Typically, gas channel ends 697 and 677 are tapered towards analyte channel 620 as shown in FIG. 6b so that the gas streams cut across the exiting analyte at spray tip 625. Depending on the composition of the analyte and other ionization conditions, gas pressure can be varied or completely turned off. Typically, applying gas assisted spray ionization produces a more stable spray, especially when an analyte with a higher water content is sprayed. As a voltage is applied to microfluidic chip 610, the sprayed droplets become charged. The charged droplets undergo a desolvation process by collision with the heated gas stream coming from channel ends 697 and 677 and the analyte ions are formed.

Figure 7A:
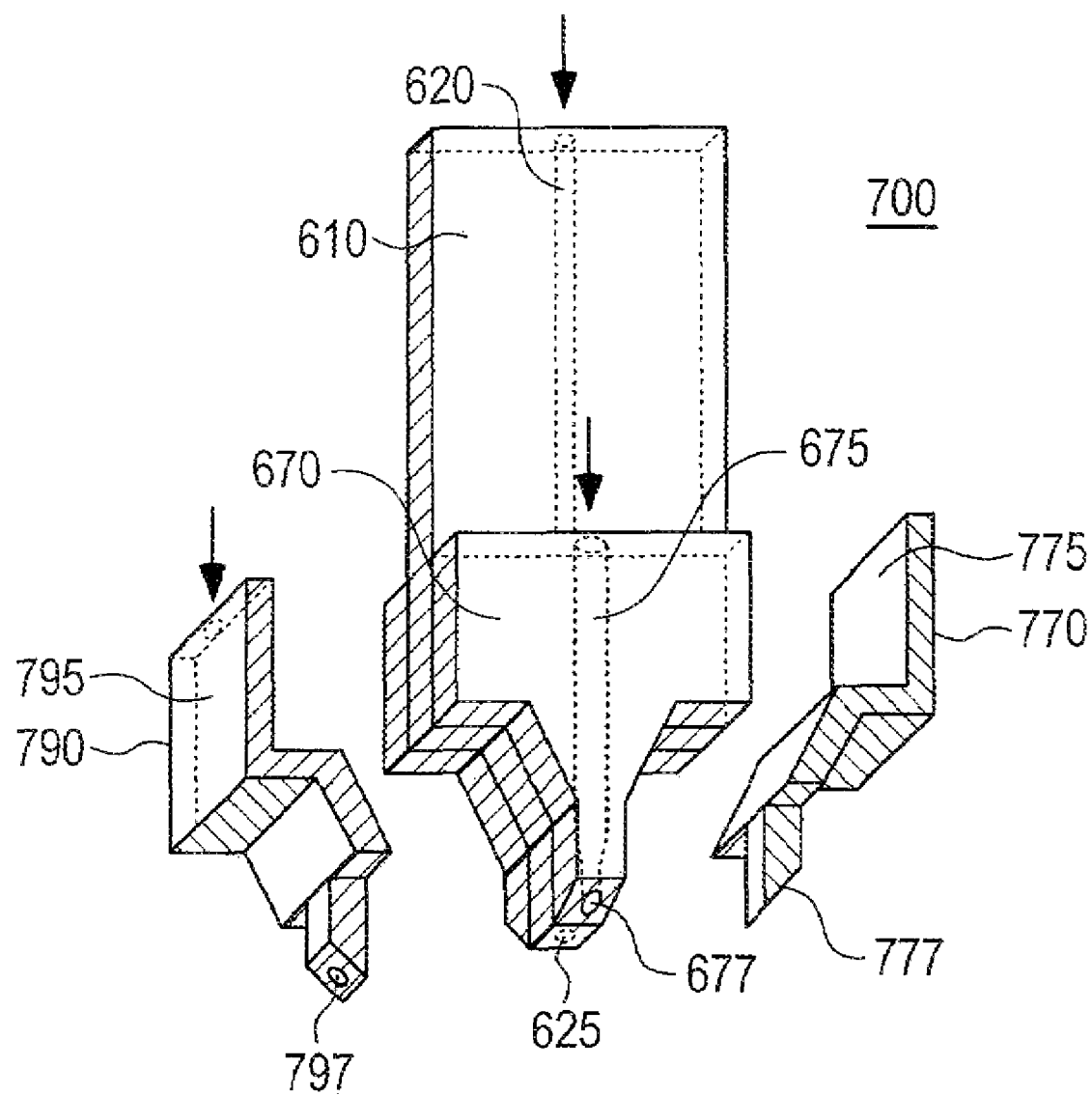
FIG. 7a shows an embodiment in accordance with the invention in an exploded view.

FIG. 7a shows an embodiment in accordance with the invention in an exploded view. In FIG. 7a, microfluidic chip 610 and auxiliary gas chips 690 and 670 are configured as shown in FIG. 6b for microfluidic electrospray structure 600 but with additional auxiliary gas chips 790 and 770 having gas channels 795 and 775, respectively. Gas channels 795 and 775 each have a gas input means. Auxiliary gas chips 790 and 770 are added in a plane perpendicular to the plane containing microfluidic chip 610 and disposed on opposite sides of microfluidic electrospray structure 600 to form microfluidic electrospray structure 700. The gas channel ends 797 and 777 are typically located about 20 μm to about 500 μm behind spray tip 625. Auxiliary gas chips 790 and 770 may be, for example, glued or laminated to microfluidic electrospray structure 600 to form electrospray structure 700. Typically, auxiliary gas chips 790 and 770 are made of a material similar to and have dimensions similar to that of microfluidic chip 610. The addition of auxiliary gas chips 790 and 770 serve to provide a gas stream on all four sides of spray tip 625. Providing four auxiliary gas chips typically results in better spray collimation and improved desolvation.

Figure 7B:
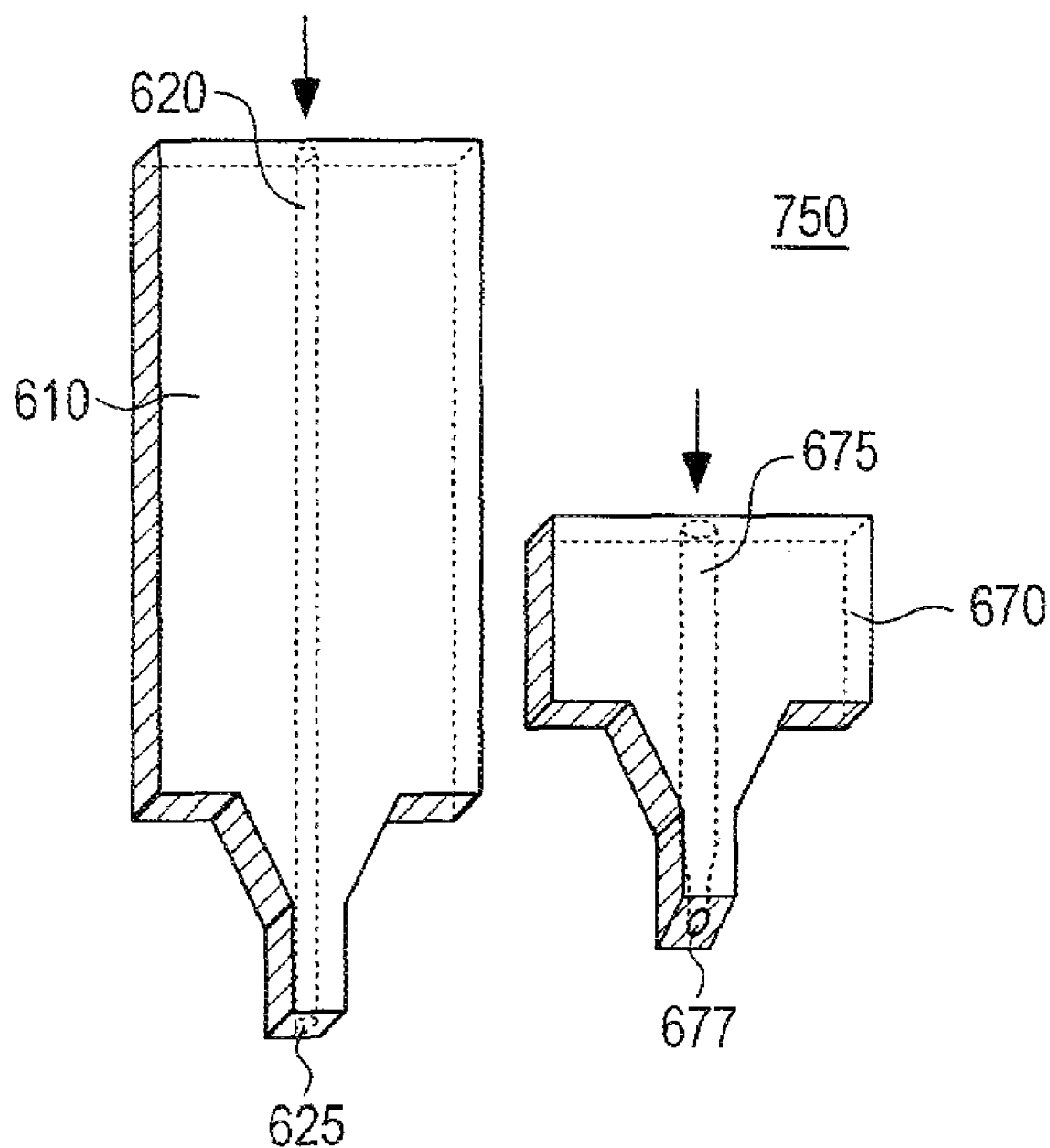
FIG. 7b shows an embodiment in accordance with the invention in an exploded view.

FIG. 7b shows an embodiment in accordance with the invention. In FIG. 7b, only auxiliary gas chip 670 is disposed on either the top or bottom of microfluidic chip 610 which provides for gas nebulization for resulting microfluidic electrospray structure 750. Gas channel end 677 of gas channel 675 is typically positioned about 20 μm to about 500 μm behind spray tip 625.

Figure 8A:
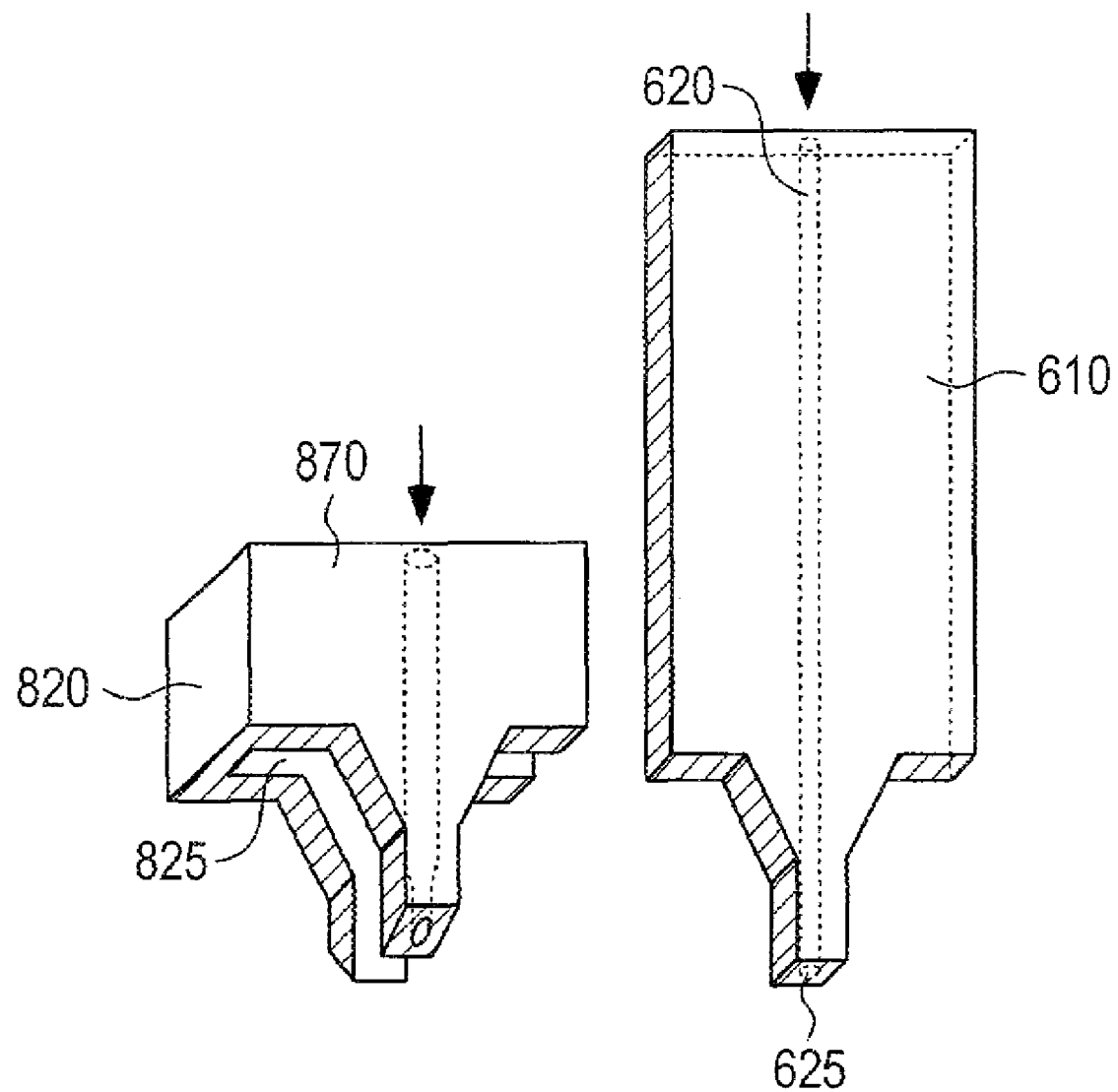
FIG. 8a shows an embodiment in accordance with the invention in an exploded view.
Figure 8B:
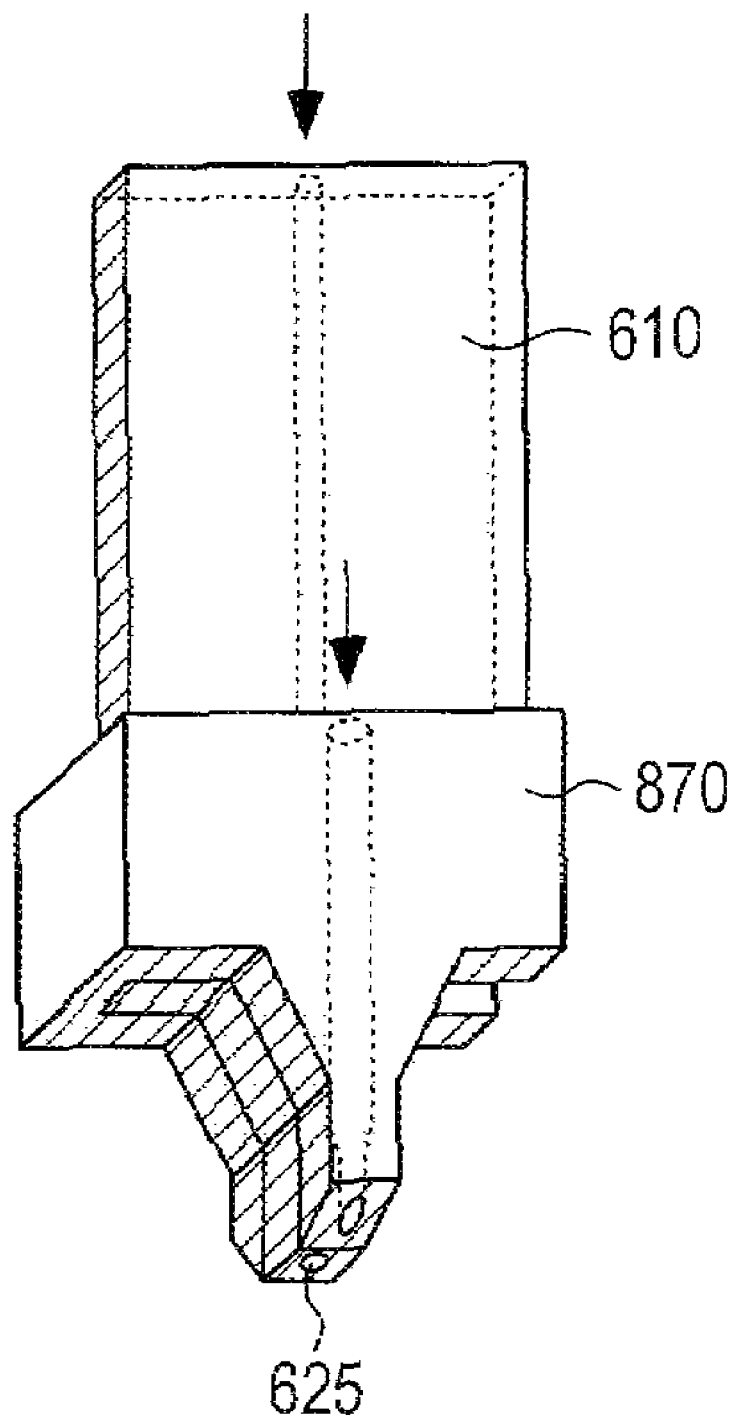
FIG. 8b shows an embodiment in accordance with the invention.

FIG. 8a shows an embodiment in accordance with the invention in an exploded view. FIG. 8a shows two auxiliary gas chips being combined to form single auxiliary gas jack 870 using connecting member 820. Auxiliary gas jack 870 may, for example, be made of materials such as steel or polymer. Auxiliary gas jack 870 has recess 825 which allows insertion of microfluidic chip 610 as shown in FIG. 8b to form microfluidic electrospray structure 800. Upper gas channel 895 and lower gas channel 875 have gas channel ends 897 and 877, respectively. Upper gas channel 895 and lower gas channel 875 typically each have gas input means. The gas channel ends 897 and 877 of gas channels 895 and 875, respectively, are typically positioned about 20 μm to about 500 μm behind spray tip 625. Gas channels 895 and 875 have dimensions similar to analyte channel 620 which is typically on the order of 50 μm in diameter but the diameters at gas channel ends 897 and 877 are typically considerably smaller, on the order of about 10 μm. Because of the smaller diameter at gas channel ends 897 and 877, a pressure drop is created at gas channel ends 897 and 877 resulting in a high speed gas stream. Typically, gas channel ends 897 and 877 are tapered towards analyte channel 620 as shown in FIG. 6b so that the gas streams cut across the exiting analyte at spray tip 625.

Referring now to FIGS. 1-5, the method of operation begins by the introduction of a sample into the analytical system 1. The sample may be first subject to separation, purification or isolation by separation system 2. After having been purified or separated into distinct components, the sample is directed through a series of channels, conduits or chambers to microfluidic chip 3, where it is received by analyte channel 15. The sample travels down analyte channel 15 until it reaches first end 9 and spray tip 10. Spray tip 10 may be maintained at atmospheric pressure, below atmospheric pressure or above atmospheric pressure. Pressure for operating the electrospray apparatus are well known and employed in the art. The sample is then sprayed out of spray tip 10 and ionized. First gas channel 17 and second gas channel 19 are used to assist the nebulization of the sample. It should be noted that certain embodiments in accordance with the invention may be designed to comprise only one gas channel. In other embodiments it can be imagined that multiple gas channels may be designed. As shown in FIGS. 1-4, the gas channels are constructed near spray tip 10. Both gas channels may be identical and arranged symmetrically on each side of spray tip 10. The gas channels may also be formed using laser ablation on central layer 13. The end of first gas channel 17 and second gas channel 19 are typically placed 20 to 500 micrometers behind the end of the analyte channel 15. First gas channel 17 and second gas channel 19 may have a similar size or dimension to the analyte channel 15. Dimensions may range from about 10 to about 200 micrometers. However, the cross-sectional area of the end of the gas channel may be considerably smaller (i.e. around 10 micrometers). Due to its smaller dimension, a pressure drop occurs at the end of the gas channels so that high speed gas stream is produced. For instance, pressure may be applied to the gas at a pressure from 5 to 100 PSI to the gas channels, gas jets are formed at the ends of the gas channels. Various gases may be employed with the present invention. For instance, air, argon, nitrogen, etc. may be employed with the present invention. The invention may utilize any number of different gases or combination of gases that are know or used in the art. The gas jets facilitate the spray ionization. Depending on composition of analyte and other ionization conditions, gas pressure can be varied or completely turned off. Generally, applying gas assisted spray ionization produced more stable sprays, especially when the solution is aqueous.

Typically, the end of the gas channel is tapered toward the analyte channel 15 as shown in the FIG. 2, so the gas stream cuts across the analyte at the spray tip 10. Voltages can be applied to either the microfluidic chip 3 or interface. Electrospray ionization is typically formed when a voltage of 1500 to 2500 volts is applied between spray tip 10 and the mass spectrometer interface (not shown). These techniques, designs and methods are well known in the art. The polarity can be adjusted based on the ion of interest. The ions that are produced by microfluidic chip 3 may then be detected by detector 7. Spray tip 10 may be maintained above atmospheric pressure, at atmospheric pressure or below atmospheric pressure to improve overall detection results and signal to noise ratios. In other embodiments, the gas introduced into analyte and/or analyte channel 15 may be employed to perform mixing, solution chemistry or solution chemical reactions.

Figure 9:
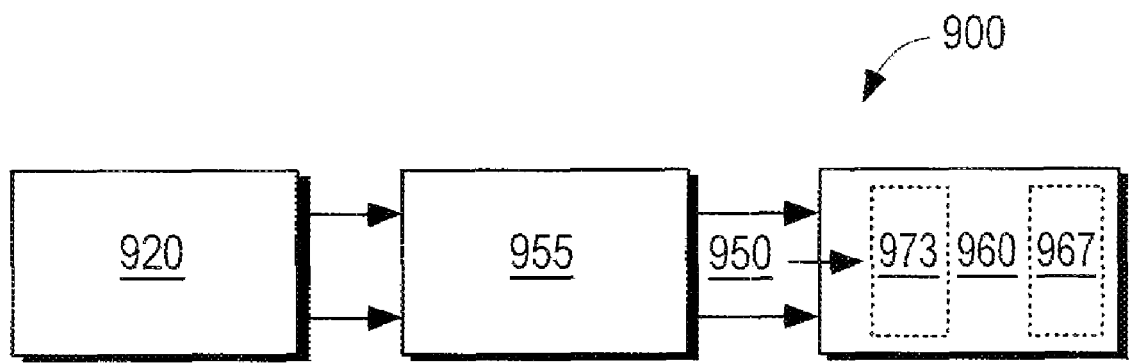
FIG. 9a general block diagram of the system in accordance with the invention.

FIG. 9 shows a general block diagram of analytical system 900 in accordance with the invention. Analytical system 900 may comprise optional separation system 920, microfluidic electrospray structure 955, an optional transport system 950 and mass spectrometry system 960. Mass spectrometry system 960 comprises mass analyzer 973 and detector 967. The block diagram is not to scale and is drawn in a general format because embodiments in accordance with the invention may be used with a variety of different types of designs and systems. In addition, each of the designs or arrangements may be changed or adjusted. The invention should not be interpreted to be limited to the illustrated embodiments. Each of the systems and/or components is described in more detail below.

Optional separation system 920 may comprise any number of systems known in the art for separating molecules. More commonly this system may comprise an analytical system such as a liquid chromatography system (LC). However, other systems and methods known in the art may be employed. For instance, the separation system 920 may also comprise an electrophoresis system and/or apparatus, an isoelectric focusing system and/or apparatus, a biorad or similar type preparative electrophoresis system and/or apparatus, an analytical or preparative column, a two dimensional gel, and other systems and/or apparatus that are known in the art for separating molecules. FIG. 9 shows an embodiment in accordance with the invention where an analytical system is employed. The analytical system, for example, comprises a high performance liquid chromatography (HPLC) microfluidic chip and associated equipment. These parts and designs are well known in the art and are, therefore, not described here in any further detail.

Transport system 950 is used for transporting ions and moving them from one location to another. Transport system 950 is typically interposed between microfluidic electrospray structure 955 and mass spectrometry system 960. However, this is not a required configuration. Microfluidic electrospray structure 955 may comprise microfluidic electrospray structure 600, 700, 750 or 800.

Transport system 950 may comprise any number of ion transporting devices known in the art. Typically, some type of skimmer or ion optics guide may also be employed in transport system 950. Transport systems 950 are well known in the art and are, therefore, not discussed in detail here.

Mass spectrometry system 960 comprises mass analyzer 973 and detector 967. Mass analyzer 973 is used for separating and determining the m/z ratio of the ions produced by an ion source. In certain instances mass spectrometry system 960 may also comprise microfluidic electrospray structure 955.

Detector 970 is positioned downstream from transport system 950 and may comprise any number of detectors known and used in the art. Some typical detectors may include photomultiplier tubes or other similar type technology. The detectors may be coupled to a computer and interface for output of the results to a third party user interface (not shown in the FIGS.).

Referring now to FIGS. 9 and 6a-8b, the method of operation begins by the introduction of a sample into the analytical system 900. The sample may be first subject to separation, purification or isolation by separation system 920. After having been purified or separated into distinct components, the sample is directed through a series of channels, conduits or chambers to microfluidic chip 610, where it is received by analyte channel 620. The sample travels down analyte channel 620 until it reaches spray tip 625. Spray tip 625 may be maintained at atmospheric pressure, below atmospheric pressure or above atmospheric pressure. Pressure for operating the electrospray apparatus are well known and employed in the art. The sample is then sprayed out of spray tip 625 and ionized. In FIGS. 6a-b, gas channels 695 and 675 in auxiliary gas chips 690 and 670, respectively, are used to assist the nebulization of the sample. In FIG. 7a, additional gas channels 795 and 775 in auxiliary gas chips 790 and 770, respectively, are added to assist the nebulization of the sample. It should be noted that certain embodiments in accordance with the invention may be designed to comprise only auxiliary gas chip 670 with gas channel 675 as shown in FIG. 7b. In other embodiments in accordance with the invention, additional auxiliary gas chips 790 and 770 with gas channels 795 and 775, respectively, are added as noted above. Gas channels 695, 675, 795 and 775 may have a similar size or dimension to the analyte channel 620. Dimensions may range from about 10 μm to about 200 μm. However, the cross-sectional area of the end of the gas channel may be considerably smaller (i.e. around 10 micrometers). Due to smaller cross-sectional area, a pressure drop occurs at the end of the gas channels so that high speed gas stream is produced. For instance, pressure may be applied to the gas at a pressure from 5 to 100 PSI to the gas channels, gas jets are formed at the ends of the gas channels. Various gases may be employed with the present invention. For instance, air, argon, nitrogen, etc. may be employed with the present invention. The invention may utilize any number of different gases or combination of gases that are know or used in the art. The gas jets facilitate the spray ionization. Depending on composition of analyte and other ionization conditions, gas pressure can be varied or completely turned off. Generally, applying gas assisted spray ionization produced more stable sprays, especially when the solution is aqueous.

Typically, the end of the gas channels is tapered toward the analyte channel 620 as shown in the FIGS. 6a-8b, so the gas stream cuts across the analyte at the spray tip 625. Voltages can be applied to either the microfluidic electrospray structure 955 or interface. Electrospray ionization is typically formed when a voltage of 1500 to 2500 volts is applied between spray tip 625 and the mass spectrometer interface (not shown). These techniques, designs and methods are well known in the art. The polarity can be adjusted based on the ion of interest. The ions that are produced by microfluidic chip 610 may then be detected by detector 970. Spray tip 625 may be maintained above atmospheric pressure, at atmospheric pressure or below atmospheric pressure to improve overall detection results and signal to noise ratios. In other embodiments, the gas introduced into analyte and/or analyte channel 620 may be employed to perform mixing, solution chemistry or solution chemical reactions.

The invention claimed is:

1. A microfluidic electrospray structure comprising: a microfluidic chip comprising an analyte channel ending in a spray tip; and a first auxiliary gas chip comprising a first gas channel having a first end, said first auxiliary gas chip disposed in contact with said microfluidic chip such that said first end of said first gas channel is adjacent to said spray tip.

2. The microfluidic electro spray structure of claim 1 further comprising a second auxiliary gas chip comprising a second gas channel having a second end, said second auxiliary chip disposed in contact with said microfluidic chip such that said second end of said second gas channel is adjacent to said spray tip.

3. The microfluidic electro spray structure of claim 2 further comprising a third auxiliary gas chip comprising a third gas channel having a third end, said third auxiliary chip disposed in contact with said microfluidic chip such that said third end of said third gas channel is adjacent to said spray tip.

4. The microfluidic electrospray structure of claim 1 wherein said analyte channel comprises a separation column.

5. The microfluidic electrospray structure of claim 1 wherein said microfluidic chip is comprised of a material selected from the group consisting of titanium, stainless steel and polyamide.

6. The microfluidic electro spray structure of claim 1 wherein said first auxiliary chip is comprised of a material selected from the group consisting of titanium, stainless steel and polyamide.

7. The microfluidic electrospray structure of claim 1 wherein said first end of said first gas channel is tapered toward said analyte channel.

8. A microfluidic electrospray structure comprising: a microfluidic chip comprising an analyte channel ending in a spray tip; and an auxiliary gas jack comprising a first gas channel having a first end and comprising a second gas channel having a second end, said auxiliary gas jack shaped to have a recess which encloses a portion of said microfluidic chip such that said auxiliary gas jack is in contact with said microfluidic chip such that said first and said second gas channel ends are adjacent to said spray tip.

9. The microfluidic electro spray structure of claim 8 wherein said analyte channel comprises a separation column.

10. The microfluidic electro spray structure of claim 9 wherein said microfluidic chip is comprised of a material selected from the group consisting of titanium, stainless steel and polyamide.

11. The micro fluidic electro spray structure of claim 9 wherein said auxiliary gas jack is comprised of a material selected from the group consisting of titanium, stainless steel and polyamide.

12. The microfluidic electrospray structure of claim 9 wherein said first end of said first gas channel is tapered toward said analyte channel.

13. A mass spectrometry system comprising: a microfluidic electrospray structure for electrospray ionization comprising a microfluidic chip and an auxiliary gas chip; and a detector downstream from said microfluidic electrospray structure for detecting ions.

14. The mass spectrometry system of claim 13 further comprising a separation system.

15. A method for electro spray ionization comprising; ejecting and ionizing a sample from a spray tip fluidly coupled to an analyte channel of a microfluidic chip; and assisting the ionization of said ejected sample by applying a gas stream from an auxiliary gas chip to said ejected sample.

* * * * *

UNITED STATES PATENT AND TRADEMARK OFFICE
CERTIFICATE OF CORRECTION

PATENT NO. : 7,642,508 B2
APPLICATION NO. : 11/680577
DATED : January 5, 2010
INVENTOR(S) : Gangqiang Li It is certified that error appears in the above-identified patent and that said Letters Patent is hereby corrected as shown below:

In column 9, line 55, in Claim 2, delete "electro spray" and insert -- electrospray --, therefor.

In column 10, line 4, in Claim 3, delete "electro spray" and insert -- electrospray --, therefor.

In column 10, line 15, in Claim 6, delete "electro spray" and insert -- electrospray --, therefor.

In column 10, line 31, in Claim 9, delete "electro spray" and insert -- electrospray --, therefor.

In column 10, line 33, in Claim 10, delete "electro spray" and insert -- electrospray --, therefor.

In column 10, line 37, in Claim 11, delete "micro fluidic" and insert -- microfluidic --, therefor.

In column 10, line 37, in Claim 11, delete "electro spray" and insert -- electrospray --, therefor.

In column 10, line 51, in Claim 15, delete "electro spray" and insert -- electrospray --, therefor.

Signed and Sealed this

Thirtieth Day of March, 2010

David J. Kappos
*Director of the United States Patent and Trademark Office*